United States Patent [19]

Ashraf-Khorassani

[11] Patent Number: 5,241,998

[45] Date of Patent: Sep. 7, 1993

[54] APPARATUS AND METHOD FOR PACKING PARTICLES

[75] Inventor: Mehdi Ashraf-Khorassani, Pittsburgh, Pa.

[73] Assignee: Suprex Corporation, Pittsburgh, Pa.

[21] Appl. No.: 784,768

[22] Filed: Oct. 30, 1991

[51] Int. Cl.$^5$ .............................................. B65D 1/08
[52] U.S. Cl. ...................................... 141/67; 141/71; 141/80; 141/81; 210/198.2; 210/656; 210/657; 210/659
[58] Field of Search ................. 141/67, 71, 80, 81, 141/100, 102, 105, 5, 9, 11, 12; 210/198.2, 656, 657, 659

[56] References Cited

U.S. PATENT DOCUMENTS

| | | | |
|---|---|---|---|
| 3,317,312 | 5/1967 | Kraus et al. | 210/656 X |
| 3,326,875 | 6/1967 | Moore | 210/656 X |
| 3,337,529 | 8/1967 | Laufer | 210/656 X |
| 3,471,261 | 10/1969 | Patterson | 210/656 X |
| 3,586,067 | 6/1971 | Bye-Jorgensen | 141/12 |
| 3,837,540 | 9/1974 | Wagener | 141/100 X |
| 4,270,921 | 6/1981 | Graas | 210/656 |
| 4,372,100 | 2/1983 | Miller et al. | 141/105 X |
| 4,483,773 | 11/1984 | Yang | 210/656 |
| 4,596,277 | 6/1986 | Djordjevic | 141/100 X |
| 4,737,292 | 4/1988 | Ritacco et al. | 210/656 |
| 4,880,543 | 11/1989 | Khosah et al. | 210/635 |
| 4,921,020 | 5/1990 | Pamper | 141/105 X |
| 4,985,143 | 1/1991 | Freeman et al. | 210/198.2 |
| 4,990,259 | 2/1991 | Kearney et al. | 210/659 |
| 4,994,180 | 2/1991 | Sims et al. | 210/198.2 |
| 5,013,433 | 5/1991 | Shalon | 210/198.2 |
| 5,043,062 | 8/1991 | Bale et al. | 210/198.2 |
| 5,080,785 | 1/1992 | Allington et al. | 210/198.2 |
| 5,089,124 | 2/1992 | Mahar et al. | 210/198.2 |
| 5,104,530 | 4/1992 | Maroldo et al. | 210/198.2 |
| 5,108,597 | 4/1992 | Funkenbusch et al. | 210/198.2 |
| 5,127,450 | 7/1992 | Saatkamp | 141/105 X |
| 5,137,627 | 8/1992 | Feibush | 210/198.2 |
| 5,141,634 | 8/1992 | Carr et al. | 210/198.2 |
| 5,141,635 | 8/1992 | LePlang et al. | 210/198.2 |
| 5,145,578 | 9/1992 | Tokubo et al. | 210/198.2 |
| 5,147,537 | 9/1992 | Sada et al. | 210/198.2 |

Primary Examiner—Stephen P. Garbe
Assistant Examiner—Stephen Cronin
Attorney, Agent, or Firm—Ansel M. Schwartz

[57] ABSTRACT

The present invention is related to an apparatus for packing an analytical chromatography column having a first opening and a second opening with packing particles. The apparatus comprises means for providing solvent at a density essentially equal to the density of the packing particles. The providing means is in fluidic communication with the first opening of the column. The apparatus also comprises a first reservoir for containing the packing particles. The reservoir is in fluidic communication with the providing means such that solvent can mix with the particles in the first reservoir to form a slurry where the particles are suspended in the solvent and agglomeration of the packing particles is essentially absent when the slurry is introduced into the analytical chromatography column. There is also valve means in fluidic communication with the first reservoir and the first opening of the analytical column for controlling flow of the slurry of pressurized solvent and packing particles to the analytical column from the first reservoir. A fluid restrictor is fluidically connected to the second opening of the column for allowing the solvent to escape from the column while maintaining pressurization therein. The invention also relates to a method of packing an analytical column with packing particles. The method comprises the steps of pressurizing a first reservoir having packing particles disposed therein, with a solvent until the density of the solvent equals the density of the particles and forms a slurry where the particles are suspended in the solvent. Then, there is the step of fluidically connecting the first reservoir to an analytical column at essentially the same pressure as the first pressure such that the slurry flows into a chamber of the analytical column.

23 Claims, 1 Drawing Sheet

APPARATUS AND METHOD FOR PACKING PARTICLES

FIELD OF THE INVENTION

The present invention is related to an apparatus and method for packing an analytical column for chromatography. More specifically, the present invention is related to an apparatus and method for packing an analytical chromatography column with particles which are suspended in a slurry to prevent aggregation and sedimentation.

BACKGROUND OF THE INVENTION

Analytical columns packed with particles or microparticulate packings are used in many chromatography instruments for the separation of components. In their optimum design, packed chromatography columns have a uniform packed bed with no cracks or channels, and without sizing or segmentation of the particles within the column. The particles are packed as densely as possible without being fractured during the packing process. Relatively large particles, such as those in the range of 30-40 $\mu$m, are typically poured into a column in a dry state. This is known in the prior art as dry-packing. Although dry-packing techniques have been used for some time, columns of high separation efficiency are more difficult to produce as particle size decreases. This is due to the fact that smaller particles have high surface energies relative to their mass, and hence tend to clump or algolorate. Such particle agglomeration causes non-uniform compaction during the packing process, which results in widely varying flow velocities along the columns channeling and thus poor column efficiency.

It is known in the prior art to use high pressure "wet fill" or slurry packing techniques to pack particles having a diameter less than 20 $\mu$m, because these small particles are difficult to form into high efficiency columns by dry-filling. In the slurry technique, a suitable liquid wets the particles and eliminates particle aggregation during packing. Proper selection of the liquid reduces the tendency of the particles to size-fractionate via gravitational sedimentation. Particles settle at a rate which is in proportion to the square of their radius and to the difference between their density and the liquid's density. This indicates that large particles settle faster than small particles. The strong dependence of settling velocity in particle size means that the wider the distribution of particle sizes, the more quickly an initially homogenous slurry of particles will become heterogenous during handling.

Thus, it is known in the prior art to use a suspending fluid that has a density equal to that of the particles. This approach is called "balanced density slurry-packing". Typically, various liquids having specific densities must be mixed in proportion to match the density of the packing particles. Once a liquid having the appropriate density is attained, it is mixed with particles to form a suspension. This suspension is then pressurized with a gas to force it into the column. The liquid is consequently drained off. This technique produces efficient columns but suffers several restrictive drawbacks. Firstly, the liquid medium typically must be produced by mixing a variety of liquids in proportion to match the specific density of the particles. This mixing and matching has been known to be a tedious process. Secondly, the liquid medium must also be matched for polarity with the particles so that aggregation due to electrical attraction and repulsion is prohibited and to prevent chemical reaction of the particles. Therefore, the liquid medium must be mixed for correct polarity. This further increases the complexity of forming the appropriate liquid medium. Thirdly, the liquid medium once matched for density and polarity is forced into the column with a pressurized gas, adding even another medium which must be in contact with the particles during packing.

The present invention offers an improved slurry-packing technique in which the suspending medium is (originally) a gas which is pressurized until its density matches that of the particles. Therefore, there is no need for mixing and matching of liquids. Further, the suspending medium does not need to be forced into the column with another pressurized medium, since the "gas" is already pressurized.

SUMMARY OF THE INVENTION

The present invention is related to an apparatus for packing an analytical chromatography column having a first opening and a second opening with packing particles. The apparatus comprises means for providing solvent at a density essentially equal to the density of the packing particles. The providing means is in fluidic communication with the first opening of the column. The apparatus also comprises a first reservoir for containing the packing particles. The reservoir is in fluidic communication with the providing means such that solvent can mix with the particles in the first reservoir to form a slurry where the particles are suspended in the solvent and agglomeration of the packing particles is essentially absent went the slurry is introduced into the analytical chromatography column. There is also valve means in fluidic communication with the first reservoir and the first opening of the analytical column for controlling flow of the slurry of pressurized solvent and packing particles to the analytical column from the first reservoir. A fluid restrictor is fluidically connected to the second opening of the column for allowing the solvent to escape from the column while maintaining pressurization therein.

In a preferred embodiment, the apparatus includes a source of solvent in fluidic communication with the providing means and the first opening of the analytical column is fluidically connected to the source of solvent through the providing means such that solvent can flow from the source to the column without passing through the valve means. Preferably, the providing means includes a three-way valve having an input port in fluidic communication with the source, a first output port in fluidic communication with the first reservoir, and a second output port. A second reservoir is in fluidic communication with the valve means, the first opening of the analytical column, and the second output port of the three-way valve such that when both output ports are open, pressure in the first reservoir, the second reservoir and the column are essentially equal. Further, when the first output port is open and the valve means is open, the slurry in the first reservoir passes to the column. Preferably, a frit is disposed in the column over the second opening.

The invention also relates to a method of packing an analytical column with packing particles. The method comprises the steps of pressurizing a first reservoir having packing particles disposed therein with a solvent until the density of the solvent equals the density of the particles and forms a slurry. The apparatus includes a source of solvent in fluidic communication with the providing means and then, there is the step of fluidically connecting the first reservoir to an analytical column at essentially the same pressure as the first pressure such that the slurry flows into the analytical column. Preferably, before the allowing step, there is the step of allowing the solvent in the column to escape. Preferably, after the connecting step, there is the step of increasing the pressure of the solvent to ensure the bed is packed densely and at the same time fully.

The present invention is also an apparatus for packing an analytical chromatography column having a first opening and a second opening with packing particles. The apparatus comprises means for providing solvent to the analytical chromatography column. The providing means is in fluidic communication with the first opening of the analytical chromatography column. The apparatus also comprises a first reservoir for containing the packing particles. The first reservoir is in fluidic communication with the providing means by way of plumbing through which the solvent can mix with the packing particles in the first reservoir to form a slurry of packing particles and solvent. Additionally, the apparatus comprises valve means in fluidic communication with the first reservoir and the first opening of the analytical chromatography column for controlling flow of the slurry to the analytical chromatography column from the first reservoir. Moreover, the apparatus comprises a second reservoir fluidically connected between the valve means and the first opening of the analytical column to ensure proper mixing of the packing particles and the solvent and a fluid restrictor fluidically connected to the second opening of the analytical chromatography column for allowing the solvent to escape from the analytical chromatography column while maintaining desired pressurization therein. Preferably, the providing means includes means for providing solvent at a density essentially equal to the density of the packing particles.

BRIEF DESCRIPTION OF THE DRAWINGS

In the accompanying drawing, the preferred embodiment of the invention and preferred methods of practicing the invention are illustrated in which.

DESCRIPTION OF THE PREFERRED EMBODIMENT

Figure 1:
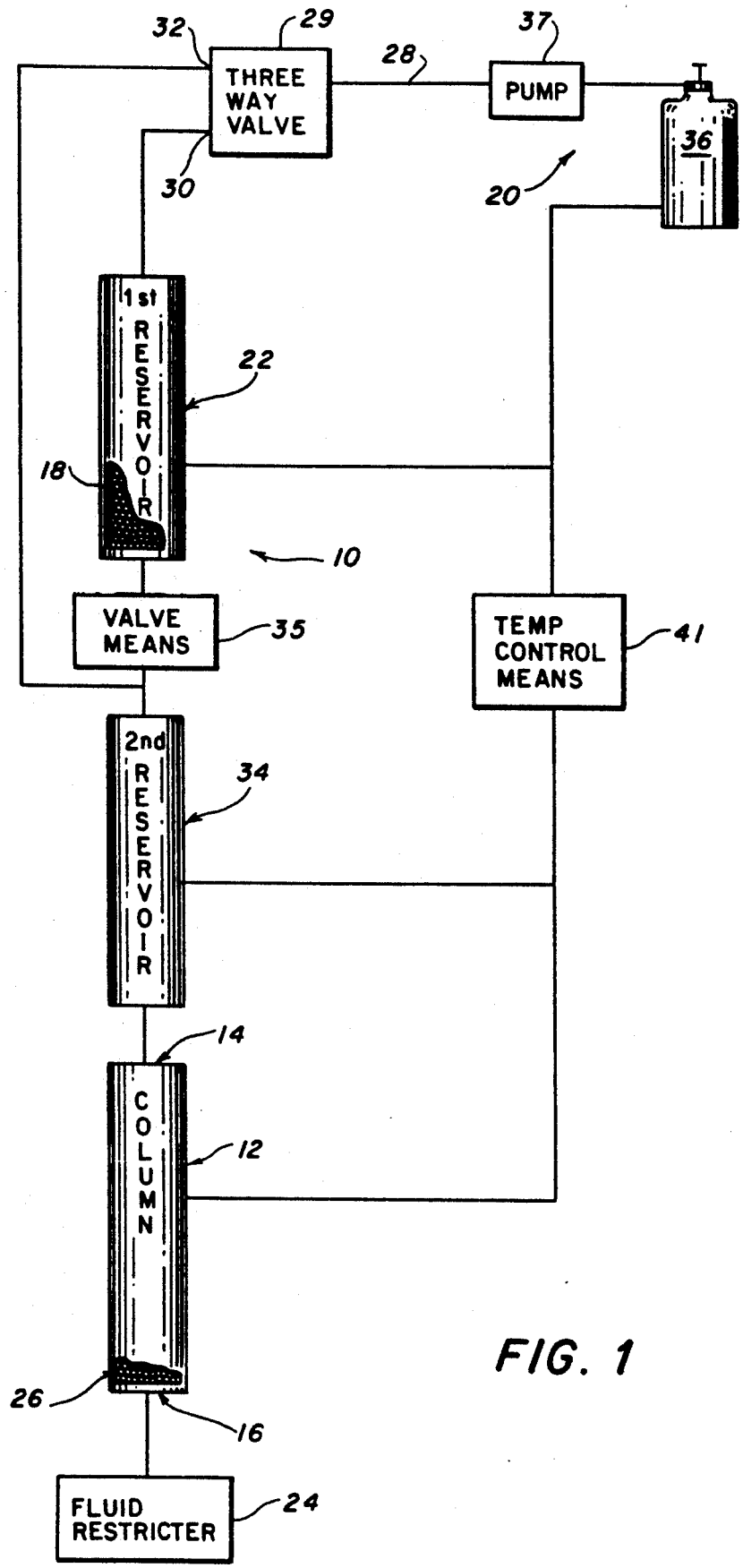
FIG. 1 is a schematic representation showing an apparatus for packing an analytical chromatography column.

Referring now to the drawings wherein like reference numerals refer to similar or identical parts throughout the several views, and more specifically to FIG. 1 thereof, there is shown an apparatus 10 for packing an analytical column 12 having a first opening 14 and a second opening 16 with packing particles 18. The apparatus 10 is comprised of means for providing solvent at a density essentially equal to the density of the packing particles 18. The providing means is in fluidic communication with the first opening 14. The apparatus also comprises a first reservoir 22 for containing the packing particles 14. The reservoir 22 is in fluidic communication with the providing means such that solvent can mix with the particles in the first reservoir from a slurry where the particles are suspended in the solvent and agglomeration of the packing particles is essentially absent when the slurry is introduced into the analytical chromatography column. There is also valve means 35 in fluidic communication with the first reservoir 22 and the first opening 14 of the analytical column 12 for controlling flow of the slurry. A fluid restrictor 24 is fluidically connected to the second opening 16 of the column 12 for allowing the solvent to escape from the column 12 while maintaining pressurization therein. The column 12 typically has an I.D. from 0.2 mm to 4.6 mm, but is not limited thereto.

In a preferred embodiment, the apparatus includes a source of solvent in fluidic communication with the providing means and the first opening 14 of the analytical column 12 is fluidically connected to the source 20 of solvent through the providing means such that solvent can flow from the source 20 to the column 12 without passing through the valve means. Preferably, the providing means includes a three-way valve 29 having an input port 28 in fluidic communication with the source 20, a first output port 30 in fluidic communication with the first reservoir 22, and a second output port 32. A second reservoir 34 is in fluidic communication with the valve means 35, the first opening 14 of the analytical column 12, and the second output port 32 of the three-way valve such that when both output ports 30, 32 are open, pressure in the first reservoir 22, the second reservoir 34 and the column 12 are essentially equal. The second reservoir insures proper mixing. Further, when the first output port 30 is open and the valve means 35 is open, the slurry in the first reservoir 22 passes to the column 12. Preferably, a frit 26 is disposed in the column 12 over the second opening 16.

The providing means, for example, can alternatively include a tank 36 of solvent pressurized at a desired pressure with a regulator controlling the release of solvent therefrom; or a pump 37 connected to a source of solvent, such as a tank 36, for pressurizing the solvent as desired. The silica particles can be, for instance, C18, C8, methyl, cyano or phenyl.

Preferably, the packing particles are made of silica and are spherically shaped having an average diameter of 10 $\mu$m, or less (3, 5 or 7 $\mu$m). The particles are preferably coated or chemically bonded with a desired material as dictated by the application.

The invention also relates to a method of packing an analytical chromatography column 12 with packing particles 18. The method comprises the steps of pressurizing a first reservoir having packing particles 18 disposed therein, with a solvent until the density of the solvent equals the density of the particles and forms a slurry where the particles are suspended in the solvent. Then, there is the step of fluidically connecting the first reservoir 22 to an analytical column 12 at essentially the same pressure as the first pressure such that the slurry flows into the analytical column. Preferably, after the connecting step, there is the step of allowing the solvent in the column to escape. Preferably, before the allowing step, there is the step of increasing the pressure of the solvent to ensure the column bed is packed densely and is fully packed. Thus, by the above, no mixing of different solvents to arrive at the desired density occurs, but is instead accomplished by varying the pressure or the temperature.

The temperature of the solvent can also be varied based on the desired density or solubility in a given application with, for instance, means for controlling temperature 41 in thermal communication with the solvent. For instance, the temperature control means can be positioned at various locations of the apparatus, as necessary, to maintain the desired temperature of the solvent during the packing of the column 12. While typically the temperature of the apparatus 10 is maintained at ambient temperature and the pressure of the solvent is varied, alternatively, the apparatus 10 could be heated or cooled to another temperature. Then, densities could again be matched as needed.

Only one type of solvent, preferably $CO_2$, which is a typically supercritical fluid at the densities used for column packing need be used. Other liquid gases such as $SF_6$ and $N_2O$ can also be used. Small amounts of additives to the $CO_2$ may be added, as required, to allow a desired polarity but the presence is not in any way for the purpose of varying the density of the solvent. If, for instance, the packing particles 18 are coated with propyl-cyanol which has a positive polarity, the $CO_2$ must be mixed with methanol, or another positive polarity compound, to raise the polarity of the pressurized $CO_2$. Adding modifier prevents aggragation of packing material. The packing particles can alternatively be coated with octane C8 or methyl C1.

In the operation of the invention, the source of pressurized solvent comprises a tank 36 of $CO_2$ pressurized in excess of 9000 PSI. The tank 36 is fluidically connected to a pump 37 which controls the pressure of the pressurized solvent flowing to the three-way valve 29. The packing particles 18 are disposed within a stainless steel first reservoir 22. The packing particles 18 have an average of 10, 5 or 3 $\mu m$ diameter and are comprised of silica and are coated with C18 (octadecyl or other stationary phases (cyano, amino, etc.). In order to match the density of these particles, the $CO_2$ must be pressurized to about 7000 PSI, at room temperature. Therefore, the pump 37 regulates the pressure of the $CO_2$, allowing it to approach to 7000 PSI. In terms of polarity, C18 is a nonpolar coating and since $CO_2$ is also nonpolar, the polarities of the $CO_2$ and the C18 ooating match. Matching the polarity of the solvent with the packing particles 18 ensures that the particles will be thoroughly wetted, and would not aggregate.

The first reservoir 22, the second reservoir 34, and the column 12 are each made of stainless steel of the pressure design necessary to contain the solvent. The first reservoir 22, the second reservoir 34 and the analytical column 12 are in fluidic communication with plumbing, such as stainless steel connectors. These connectors are designed with a minimum of dead space, having no unswept corners or pockets that can act as miniature mixing vessels. The three-way valve 29 selectively connects the pressurized $CO_2$ to the first reservoir 22. The three-way valve 29 also selectively connects the pressurized $CO_2$ to the second reservoir 34 such that the pressurized $CO_2$ can also fill both the second reservoir 34 and the analytical column 12 prior to the opening of the second valve means. In this way, the pressure across the first reservoir 22, second reservoir 34, end column 12 is maintained essentially the same. This further provides even packing of the column 12. By maintaining the valve means 35 closed at first, the pressure of the solvent is allowed to reach a desired level in the first reservoir 22 so the particles are properly suspended in the solvent.

Once the pressurized $CO_2$ is at 7000 PSI and thus essentially equals the density of the packing particles 18, a slurry is formed of packing particles suspended in the pressurized $CO_2$ in the first reservoir 22. Since the density of the $CO_2$ and the packing particles match, there is no sedimentation or agglomeration.

After the first and second reservoirs 22, 34 and the analytical column 12 are filled with $CO_2$ at about 7000 PSI, the valve means 35, which is a simple two-way valve, is opened to allow the slurry of packing particles suspended in the pressurized $CO_2$ to pass through the second reservoir 34 and into the column 12. A stainless steel frit 26 is used for covering the second opening 16 of the column 12 and prevents the particles from escaping the column but allows the $CO_2$ to escape the column 12. Then, the second reservoir 34 and the analytical column 12 are fluidically disconnected from the source of pressurized $CO_2$ by way of the second output port 32 of the three-way valve being closed. The fluid restrictor 24 allows the $CO_2$ to escape from the column 12 such that a flow is established through the first reservoir 22, second reservoir 34 and column 12. This flow causes the packing particles 18 to pass from the first reservoir 22 and be packed within the column 12.

Once the column 12 is filled to capacity with slurry, the regulator 37 is further opened to allow the $CO_2$ to be pressurized to 9000 PSI. This added pressure allows even more packed particles to enter the column 12 to be densely and fully packed. To ensure that the column 12 has enough particles to be fully packed, the first reservoir 22 holds 15% more packing particles 18 than the analytical column 12 can hold.

Once the analytical column 12 has continuously received $CO_2$ at 9000 PSI for approximately 45 minutes, the analytical column 12 is fluidically disconnected from the source 20 of pressurized $CO_2$ by the first output port 30 of the three-way valve being closed. The $CO_2$ remaining in the column 12 escapes through the fluid restrictor 24. After 4-5 hours, the packed analytical column 12 is removed from the second reservoir 34 and the fluid restrictor 24 and a second porous stainless steel frit is disposed about the column's first opening 14 and attached thereon with a stainless steel end connector.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for packing an analytical chromatography column having a first opening and a second opening with packing particles comprising:

means for providing solvent at a density essentially equal to the density of the packing particles, said providing means in fluidic communication with the first opening of the analytical chromatography column;

a first reservoir for containing said packing particles, said first reservoir in fluidic communication with the providing means by way of plumbing through which the solvent can mix with the packing particles in the first reservoir to form a slurry where the packing particles are suspended in the solvent and agglomeration of the packing particles is essentially absent when the slurry is introduced into the analytical chromatography column;

valve means in fluidic communication with the first reservoir and the first opening of the analytical chromatography column for controlling flow of the slurry to the analytical chromatography column from the first reservoir; and a fluid restrictor fluidically connected to the second opening of the analytical chromatography column for allowing the solvent to escape from the analytical chromatography column while maintaining desired pressurization therein.

2. An apparatus as described in claim 1 including a source of solvent in fluidic communication with the providing means.

3. An apparatus as described in claim 2 wherein the first opening of the analytical column is fluidically connected to the source of pressurized solvent through the providing means causing the pressurized solvent to flow from the source to the analytical chromatography column without passing through said valve means.

4. An apparatus as described in claim 3 wherein the providing means includes a three-way valve having an input port in fluidic communication with the source, a first output port in fluidic communication with the first reservoir, and a second output port; and including a second reservoir in fluidic communication with the valve means, the first opening of the analytical column, and the second output port of the three-way valve by way of plumbing when both output ports are open, pressure in the first reservoir, the second reservoir and the column are essentially equal, and when the first output port is open and the valve means is open, the slurry in the first reservoir passes to the column.

5. An apparatus as described in claim 4 wherein the packing particles are made of silica.

6. An apparatus as described in claim 5 wherein the packing particles are spherically shaped having an average diameter less than 10 $\mu$m.

7. An apparatus as described in claim 6 wherein the solvent comprises $CO_2$ pressurized between 7000 PSI and 9000 PSI.

8. An apparatus as described in claim 7 including means for controlling the temperature of the solvent, said temperature controlling means in thermal communication with the solvent.

9. An apparatus as described in claim 7 wherein the analytical chromatography column has an inside diameter of between 0.2 and 4.6 mm.

10. An apparatus as described in claim 6 wherein the solvent is comprised of one or more from the following groups, $SF_6$, $N_2O$ and $CO_2$, maintained in the supercritical state.

11. An apparatus as described in claim 10 wherein the particles are coated or chemically bonded with a desired material to perform a chemical separation.

12. An apparatus as described in claim 11 including a frit disposed in the column over the second opening which allows the solvent to escape but prevents the particles from escaping the column.

13. An apparatus as described in claim 12 including means for controlling the pressure of the solvent, said pressure controlling means in fluidic communication with the solvent.

14. An apparatus as described in claim 13 wherein the pressure controlling means comprises a tank of solvent pressurized at a desired pressure.

15. An apparatus as described in claim 13 wherein the pressure controlling means comprises a pump.

16. An apparatus as described in claim 12 wherein the solvent includes at least one modifier to adjust its polarity to match the polarity of the packing particles.

17. An apparatus as described in claim 16 wherein the modifier comprises methanol.

18. An apparatus as described in claim 16 wherein the providing means includes a pump connected to a tank of solvent which pumps the solvent at a desired pressure to the input port of the three-way valve.

19. An apparatus as described in claim 18 wherein the silica particles are chemically bonded with one or more from the following group, C18 C8, methyl, cyano and phenyl.

20. An apparatus for packing an analytical chromatography column having a first opening and a second opening with packing particles comprising:

means for providing solvent to the analytical chromatography column, said providing means in fluid communication with the first opening of the analytical chromatography column;

a first reservoir for containing said packing particles, said first reservoir in fluidic communication with the providing means by way of plumbing through which the solvent can mix with the packing particles in the first reservoir to form a slurry of packing particles and solvent;

valve means in fluidic communication with the first reservoir and the first opening of the analytical chromatography column for controlling flow of the slurry to the analytical chromatography column from the first reservoir;

a second reservoir fluidically connected between the valve means and the first opening of the analytical column to ensure proper mixing of the packing particles and the solvent; and a fluid restrictor fluidically connected to the second opening of the analytical chromatography column for allowing the solvent to escape from the analytical chromatography column while maintaining desired pressurization therein.

21. An apparatus as described in claim 20 wherein the providing means includes means for providing solvent at a density essentially equal to the density of the packing particles.

22. An apparatus as described in claim 21 wherein the providing means includes means for controlling the temperature of the solvent, said temperature controlling means in thermal communication with the solvent.

23. An apparatus as described in claim 22 wherein the providing means includes means for controlling the pressure of the solvent, said pressure controlling means in fluidic communication with the solvent.

* * * * *